(12) United States Patent
Gäbler

(10) Patent No.: US 7,208,187 B2
(45) Date of Patent: Apr. 24, 2007

(54) CLIMATE CONTROL FOR THE TRANSPORT AND STORAGE OF PERISHABLES

(76) Inventor: Ralph Gäbler, Brueghelstrasse 4, 53757, Sankt Augustin (DE)

( * ) Notice: Subject to any disclaimer, the term of this patent is extended or adjusted under 35 U.S.C. 154(b) by 465 days.

(21) Appl. No.: 10/239,224

(22) PCT Filed: Mar. 20, 2001

(86) PCT No.: PCT/DE01/01064

§ 371 (c)(1), (2), (4) Date: Dec. 17, 2002

(87) PCT Pub. No.: WO01/71258

PCT Pub. Date: Sep. 27, 2001

(65) Prior Publication Data

US 2003/0150334 A1    Aug. 14, 2003

(30) Foreign Application Priority Data

Mar. 20, 2000   (DE) ............................... 100 13 501

(51) Int. Cl.
A23B 7/152   (2006.01)
(52) U.S. Cl. .................. 426/231; 426/312; 426/316; 426/615; 426/419; 99/468; 73/23.2
(58) Field of Classification Search .......... 99/467–468, 99/473; 426/231, 312, 316, 320, 515, 418–419; 73/23.2–31.07
See application file for complete search history.

(56) References Cited

U.S. PATENT DOCUMENTS 4,599,889 A * 7/1986 Pateras Pescara de Castelluccio .......... 73/25.01
4,829,774 A * 5/1989 Wassibauer et al. .......... 62/78

(Continued)

FOREIGN PATENT DOCUMENTS

DE    44 24 170 C1    2/1996

(Continued)

OTHER PUBLICATIONS

Jacquinot et al. Amperometric detections of gaseous ethanol and acetaldehyde at low concentrations on an Au-Nafion electrode. Mar. 9, 1999. The Analyst. http://library.eawag.ch/EAWAG-Publications/pdf/eawag_02681.pdf.*

(Continued)

*Primary Examiner*—Drew Becker
(74) *Attorney, Agent, or Firm*—Banner & Witcoff, Ltd.

(57) ABSTRACT

Method for the control of a controlled atmosphere for the storage of plant products in at least one storage- or transport space, where
 a) the concentration of at least one trace gas that is produced by the plant products and has a share of less than 1% of the controlled atmosphere is measured at least twice at different times;
 b) the degree of change in the concentration of the trace gas is derived from at least two measuring values as the measure of the production rate of the plant product for said trace gas;
 c) the control variables for the composition in the controlled atmosphere are determined depending on the degree of change in the concentration of the trace gas, and
 d) the composition of the controlled atmosphere is adjusted according to the control variables.

21 Claims, 3 Drawing Sheets

U.S. PATENT DOCUMENTS

| | | | | |
|---|---|---|---|---|
| 4,961,322 A | * | 10/1990 | Oguma et al. | 62/179 |
| 5,163,360 A | * | 11/1992 | Petz | 99/468 |
| 5,419,153 A | * | 5/1995 | Hartley | 62/408 |
| 5,791,236 A | * | 8/1998 | Schouten | 99/468 |
| 6,711,470 B1 | * | 3/2004 | Hartenstein et al. | 700/276 |

FOREIGN PATENT DOCUMENTS

| | | | |
|---|---|---|---|
| EP | 0749692 A2 | * | 12/1996 |
| JP | 60190838 | * | 9/1985 |
| JP | 360190838 A | * | 9/1985 |
| JP | 04158739 A | * | 6/1992 |
| JP | 2002-235979 A | * | 8/2002 |
| SU | 1250210 A | * | 8/1986 |
| SU | 1250210 A1 | * | 8/1986 |

OTHER PUBLICATIONS

Oomens et al. CO-laser-based photoacoustic trace-gas detection: applications in postharvest physiology. May 13, 1998. Applied Physics B. http://library.eawag.ch/EAWAG-Publications/pdf/eawag_02681.pdf.*

Belitz, H.-D., Grosch, W.: Lehrbuch der Lebensmittelchemie. 3. R. Aufl., Berlin u.a., Springer Verlag, 1987, pp. 672-676.

* cited by examiner

CLIMATE CONTROL FOR THE TRANSPORT AND STORAGE OF PERISHABLES

FIELD OF INVENTION

The invention relates to a method for the control of a controlled atmosphere for the storage of plant products in at least one storage- or transport space.

BACKGROUND

So as to have a variety of plant products such as fruit, vegetables and fresh flowers available in every country and during all seasons, regardless whether or not these products are raised in that particular country during the respective season, or even at all, there is a strong desire to create appropriate transport- and storage conditions for these products so that they can be stored for a prolonged period of time immediately following the harvest, and can still be sold to the consumer as fresh products without any loss of quality. Under appropriate conditions, the rather expensive transport of individual container units via airfreight can be replaced by the significantly more cost-efficient mass transport per sea freight. Furthermore, the longer storage times eliminate the fluctuating supply as a result of harvesting cycles.

The principal problem in the storage of plant products over a prolonged period of time is that they are living organisms with a metabolism and an energy requirement, whereby said metabolism must be maintained during storage.

By means of targeted manipulation, such as lowering the temperature, controlling the air humidity, a significant increase of the $CO_2$-concentration and lowering the $O_2$-concentration in the atmosphere of the storage facility, for example, the activity of the enzymes taking part in the breathing metabolism is lowered and thus the metabolism of the fruit is delayed during storage. Another advantage of this type of controlled atmosphere is that feeding pests in the storage spaces are exterminated. With fruit, one differentiates between climacteric fruits such as bananas, kiwis, tomatoes or apples, and non-climacteric fruits such as citrus fruits, for example. They are different in that they react differently to the composition of the atmosphere, and the plant hormone ethylene plays a different role during their ripening process.

The metabolism of plant products and fruits cannot be lowered any by lowering the $O_2$-concentration. When the concentrations are too low, the energy that the plant product requires for metabolism is generated by a conversion to alcoholic fermentation, which causes the generated alcohol to accumulate in the stored product, leading to a drastic loss of quality.

An increased $CO_2$-concentration during storage can influence the normal metabolism of the fruit with respect to storage positively in view of the glycolysis, the fermentation, the cancer cycle or the electron transport. However, their breathing hardly decreases in the pre-climacteric, whereas a significant reduction can be detected for climacteric fruit in the climacteric. On the other hand, for example, the peel of apples may scald [turn brown] if the $CO_2$-concentration is too high and the storage temperatures are low, which renders the apples unfit for sale. Although adding antioxidants can reduce the degree of scalding, this type of treatment is not permitted in Germany. Furthermore, an excessive $CO_2$-concentration can also lead to an increased $C_2H_4$-production, irregular ripening, suppressed or more difficult physiological processes and an increased susceptibility for rotting.

Ethylene is a plant hormone that plays a key role in a great number of various growth phases and -processes of plants and fruit, such as germination, sprout growth, flowering, wilting, ripening of the fruit, senescence, etc. However, it is also produced by the plants in stress situations such as a lack of water, over-flooding, heat, coldness, fungus- and bacteria attacks and mechanical injury.

The so-called Yang cycle describes the biosynthesis of the ethylene:

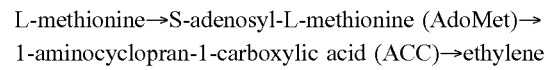

L-methionine→S-adenosyl-L-methionine (AdoMet)→ 1-aminocyclopran-1-carboxylic acid (ACC)→ethylene The enzymes that are relevant for the control of the ethylene production are the ACC synthase, i.e., the conversion from AdoMet to ACC, and the ACC oxidase, the oxidation from ACC to ethylene.

Thus, one takes advantage of the influence of ethylene on the ripening process of climacteric fruits. In this way, the ripening process can be irreversibly induced by exogenous ethylene in the atmosphere surrounding the fruit. For example, the ethylene content in the atmosphere of the storage space is increased by a multiple shortly before the sale of stored, unripe bananas to bring the bananas to a full ripeness.

Lower temperatures—so-called cold stress—stimulates the autocatalytic ethylene production in climacteric fruits. The ethylene induced by cold stress is generated in the course of normal biosynthesis (Yang cycle), whereby the conversion capacity from ACC to $C_2H_4$ increases as the temperature drops.

EP 0 703 727 B1 discloses a method for the transport of quickly perishable goods, especially freshly harvested, unripe bananas, where the bananas are first stored in a shipping- and ripening container and brought to a temperature of 14 to 15° C. in said container. To initiate the ripening process of the bananas, the bananas are gassed with ethylene for up to 48 hours. Then the atmosphere containing ethylene is displaced by a controlled atmosphere with a reduced oxygen content of 2% to 10%, whereby a minimum ethylene content that is sufficient to support a continuous ripening process is supposed to be retained. Finally, normal atmospheric conditions are restored in the container and the bananas are unloaded.

In addition, WO 86/01296 discloses a detector for the verification of ethylene in the storage of the transport of plant products. Said detector is supposed to determine when an ethylene limit value has been reached in the storage facility, so that the storage facility can be aerated by turning on a ventilator, and the ethylene concentration can be lowered in this way. Specifically, this is supposed to reduce the energy costs created by the continuous aeration of the storage space for a permanent discharge of the ethylene emitted by the products. The detector is also supposed to be used to check the concentration of ethylene in the atmosphere of the storage room when ethylene is added to the atmosphere to speed up the ripening process.

With all known methods, however, it cannot be avoided that some of the plant products perish. For one, this is attributed to the fact that the quality at the time of storage and during the course of the storage or the transport is not known.

SUMMARY

Proceeding on the aforementioned, the problem to be solved by one skilled in the art is to provide a method of the type mentioned initially, where changes in the ripening process of the products to be transported are recognized early, and the controlled atmosphere can be adjusted accordingly to retain the freshness of the products as much as possible.

This problem is solved with a method for the storage of plant products of the type mentioned initially, where
 a) the concentration of at least one trace gas that is produced by the plant products and represents less than 1% of the controlled atmosphere is measured at least twice at different times,
 b) the degree of change in the concentration of the trace gas is derived from the sequence of at least two measuring values as the measure of the production rate of the plant product for said trace gas,
 c) the control variables for the composition of the controlled atmosphere are determined depending on the degree of change in the concentration of the trace gas, and
 d) the composition of the controlled atmosphere is adjusted corresponding to the control variables.

BRIEF DESCRIPTION

Figure 1:
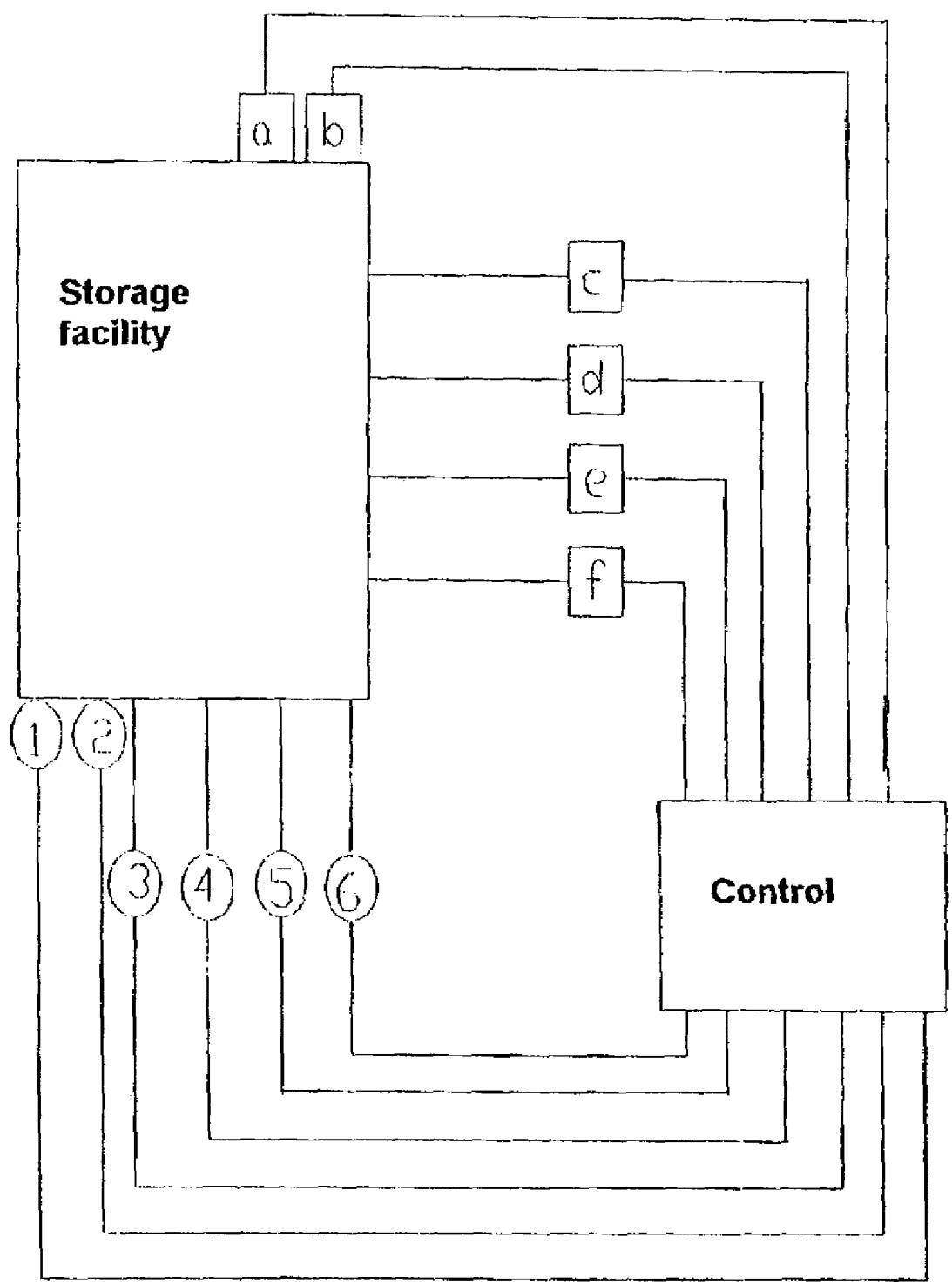
FIG. 1 shows a control system for a storage space.

By determining the degree of change in the concentration of trace gases, it is possible to keep a record of the ripening- or quality condition of the plant products stored in the storage- or transport space. This also takes advantage of the fact that in addition to $CO_2$, other trace gases are generated as well as a result of the metabolism of the plant products. The change in the concentration of these trace gases, which are generally produced in very low quantities, can be detected relatively easy in the controlled atmosphere because very small quantities of generated trace gases already significantly increase the concentration of the respective trace gas in the controlled atmosphere; their concentration is usually less than 0.01%. The production rate of such trace gases then allows conclusions about the ripeness condition of the stored plant products.

Highly sensitive gas detection systems are used to measure the gas concentrations. At least two measurements of the concentration of the trace gas at two different times are required to be able to determine a change in the concentration, whereby the production rate of the plant products for said trace gas is determined as a derivation of the concentration behavior over time.

The measured values can be compared to empirically determined values for the production rates of trace gases of various plant products, and from the result, an atmosphere composition that is optimized for the respective degree of ripeness or condition of the plant products and the planned travel- or transport time can be set.

Depending on the determined ripening condition, a composition of the controlled atmosphere that is advantageous for the storage is determined, whereby the composition can always be readjusted to the condition of the plant products. In that way, in particular the concentrations of $CO_2$ and $O_2$ to be adjusted can be determined in the controlled atmosphere and optimized regularly for the desired degree of ripeness of the plant products. For example, especially with fruits, a lowering of the $O_2$-concentration and a simultaneous increase of the $CO_2$-portion in the atmosphere leads to a reduced metabolism of the plant products.

Proceeding from a pre-adjusted controlled atmosphere, it is possible on the one hand to react to a change in the condition of the plant products as determined by the measurement by adjusting the composition of the controlled atmosphere to the respective degree of ripeness of the stored plant products by changing the pre-set concentration of one or more gas components of the controlled atmosphere and/or humidity and/or temperature by a specific measure when one degree of change is detected in the concentration of a specific plant product, i.e., the degree of change of the control variables for adjusting the controlled atmosphere depends directly on the degree of change in the concentration of a trace gas.

On the other hand, a determined degree of change in the concentration of one or more trace gases according to a known pattern, which is stored in the look-up table of a control computer, can be compared. If the degree of change in the concentration coincides—at least largely—with a pattern, the control variables that can be called up and used to set the controlled atmosphere are control variables that were saved in the computer for that specific pattern. Such sets of control variables are based on empirically determined storage parameters that are ideal for a specific condition of a plant product. In this process, the ideal storage parameters for a specific degree of ripeness with respect to the composition of the controlled atmosphere, including the temperature- and humidity values for various plant products, are generally different, and the ideal storage parameters may be different even for the same plant product from various regions or origin, or with different respective courses of the growth period.

Methods for adjusting the composition of the controlled atmosphere with specified control variables are sufficiently known to one skilled in the art and will not be discussed here in greater detail.

Monitoring of the degree of ripeness of the plant products leads to an enormous benefit for the transportation company as well as for the trade with the products to be transported. For one, the energy costs for controlling the climate in the storage/transportation spaces can be lowered significantly, and on the other hand, the quality of the products can be optimized because of a better control of the ripening process, and the waste of rotten or overripe products due to spoilage can be reduced to a minimum.

Trace gases especially suitable for determining the condition of the plant products are trace gases having a concentration of less than 0.01% in the controlled atmosphere.

Thus, an especially suitable value for determining the degree of ripening of the plant products is the degree of change in the concentration of the $C_2H_4$-concentration. In addition to the low underground concentration of the ethylene in the storage space, another advantage of a continuous monitoring of the ethylene is the key function of the ripening hormone ethylene in the ripening process of the plant products. Especially for climacteric fruits, the production rate of ethylene is a significant parameter of the degree of ripeness. In the pre-climacteric, the fruits produce only small quantities of the plant hormone, whereas the respiration rate as well as the production rate of the ethylene increase strongly during the climacteric and control the ripening process. With a very accurate detection of the ethylene production of the plant products, it is therefore possible to react quickly and effectively on developing ripening processes and change the room atmosphere accordingly. In the case of an increased production rate of the ethylene, for example, which indicates an accelerated ripening process of the stored plant products, the $O_2$-concentration in the controlled atmosphere can be lowered further if the objective is to inhibit the ripening process of the plant products. Vice versa, the $O_2$-concentration and/or the ethylene concentration in the controlled atmosphere can be increased further if the objective is to accelerate the ripening process of the plant products at the end of the storage time, and a relatively low production rate of the plant products for ethylene indicates that the ripening process does not yet have the desired speed.

During storage, it is desired to minimize the metabolism of the plant products to prolong the storage time as much as possible. However, when the $CO_2$-concentration is high and the $O_2$-concentration is low in the controlled atmosphere, the transition from oxidative to fermentative metabolism is a very narrow line, which can lead to necrotic spots and colorless tissue in plant products. In that case, the detection of $C_2H_5OH$ allows an early warning to change the storage parameters and thus maintain the quality of the fruit. To that end, the monitoring of the degree of change in the concentration of this trace gas is also of special advantage. Even the detection of small concentrations of ethanol is clear proof of the alcoholic fermentation in the stored plant products. To stop the fermentation, the $O_2$-concentration in the controlled atmosphere is then increased.

Measuring the ethane content in the controlled atmosphere can also be of significant advantage. An increasing $C_2H_6$-concentration in the controlled atmosphere, for example, indicates an irreversible damage to the tissue of the plant products. This is because the production of ethane is not a metabolic process, but solely a degradation process of organic material such as cell walls or tissue. This can have varied causes, such as low temperatures, radical reactions, lipid peroxidation, etc. Thus, if a change in the ethane concentration in the controlled atmosphere is detected, immediate action can be taken by either reducing said concentration, especially in the case of a high $CO_2$-concentration in the controlled atmosphere, and/or by increasing the temperature in the case of low storage temperatures. Other trace gases that should be mentioned are especially aldehyde, especially acetaldehyde. Like the detection of ethanol in the atmosphere, the detection of acetaldehyde also indicates fermentation processes in the plant products, with the result that the composition of the controlled atmosphere is then changed, especially by increasing the $O_2$-concentration.

It can furthermore be of advantage to determine the degree of change in the $CO_2$-concentration in the atmosphere at those times when a specific increase of the $CO_2$-concentration in the controlled atmosphere is not required in the storage of plant products. This provides conclusions about the respiration rate of the plant products and thus about their metabolic activity. With this information, it can be determined if the composition of the controlled atmosphere should be changed to accelerate or inhibit the metabolic activity.

When the degree of ripeness of the stored plant product or the plant product to be stored has been determined, it can be used to control the composition of the controlled atmosphere, whereby especially the $CO_2$-concentration, the $O_2$-concentration, the room temperature and/or the air humidity are controlled.

If an increase of the $CO_2$-concentration is desired, it may be sufficient to allow it to rise to the desired control variables with the $CO_2$ produced by the metabolism of the plant products. Likewise, the relative air humidity can be increased with the humidity emitted by the plant products. In this way, it is possible to achieve an adjustment of the climate conditions in the storage- or transport space in a time period of 24 to 36 hours.

It is especially preferred to control the $C_2H_4$-concentration in the atmosphere. Ethylene in the atmosphere, regardless of its origin, whether it is stress ethylene or ripening ethylene produced by the plant products, or gas emission from other materials in the storage space, can induce the ripening process of climacteric fruit. Thus, it is of crucial importance to keep the concentration low if the ripening process is supposed to be inhibited or at least supposed to be suppressed, and to elevate the concentration if the ripening process is supposed to be induced.

In addition to controlling the atmosphere in the entire storage space, it is also possible, with knowledge of the respective degree of ripening of the plant products, to store plant products with the same degree of ripening in close proximity to one another in the storage- or transport space.

During the growth period of the fruits, a suitable harvesting time for a plantation and/or growing region is determined based on the properties of the plants and/or fruit, such as acid content, color, sugar content, etc. and appropriate empirical values. Because of the natural ripening variation between the plants, but also because of preferred positions of the fruit within/on a plant, fruit does not have a uniform degree of ripeness. Thus, it is possible that some fruits, because of their degree of ripeness, already have a higher production rate of ethylene than other fruits. However, because ethylene can principally accelerate a ripening process significantly, it is desired, for example, to separate fruits that produce ethylene from the rest of the fruit. This allows a maximum storage time for a large part of the fruit to be stored, and decreases the waste of spoiled and/or over-ripe fruit significantly during the storage time.

The mean degree of ripeness in this context is the mean degree of ripeness of a quantity of stored plant products, with the degree of ripening of the individual fruits being more or less randomly scattered around said mean degree of ripeness. This results in a specific ripening distribution of the stored fruit which, depending on the distribution, has a specific width. For each degree of ripening, there is principally an ideal set of storage parameters that optimally maintains the storage quality of the fruit.

The optimal storage parameters of the fruit with degrees of ripeness in close proximity differ slightly, so that the metabolism can be influenced in a similarly positive way in similar ambient conditions. A wide spread in the ripeness distribution means that more fruit is not stored under optimal storage conditions.

Thus, it is of advantage if the individual degree of ripeness of individual plant products or a mean degree of ripeness of parts of the load in the storage space is determined continually or intermittently. This makes it possible to adapt the atmosphere in the various areas of the storage space to the condition of the plant products stored there, which can lead to a non-uniform composition of the atmosphere across the storage space.

With knowledge of the mean degree of ripeness of a partial quantity of the stored plant products, or with knowledge of the degree of ripeness of respective individually stored plant products, said products can be sorted according to their degree of ripeness during the storage.

One option here is to sort the fruit according to its rate of ethylene production. Thus, the mean distribution of ripening is narrowed, which enables an optimal adaptation of the climate parameters in the respective part of the space.

Especially, it is possible to sort the plant products in form of a distribution to various chambers and/or storage spaces with an atmosphere that is optimal for the respective ripening condition. In that case, there is a multiple of closed spaces with different storage atmospheres, and each plant product is stored in the chamber that has the most favorable atmospheric composition for the planned ripening process. In that case, the climate conditions within one storage space can be kept constant.

An especially suitable method for the detection of trace gases in the atmosphere of the storage space is a gas analysis process based on the photo-acoustic effect. For one, this includes a photo-acoustic detection where an acoustic wave that is generated by a periodic warming of the gas mixture, is recorded by means of a microphone and is then analyzed. It also includes, however, the so-called photo thermal deflection method, where the change in the breaking index of the gas mixture is determined based on a periodic warming with a position-sensitive diode and a visible laser beam.

Photo-acoustic sensors that are suitable for the method are described in:

1) T. Fink et al., An improved $CO_2$ laser intra-cavity photo-acoustic spectrometer for trace gas analysis, Review of Scientific Instruments, Vol. 67, No. 11, November 1996, pages 4000 to 4004, and
2) F. Harren et al., Sensitive intra-cavity photo-acoustic measurements with a $CO_2$ wave guide laser, Applied Physics, Volume 50, 137 (1990).

With this method it is possible, for example, to detect even miniscule quantities of ethylene in a range of up to 100 parts per trillion in the atmosphere of a storage- or transport space. Thus, it is possible to register even the smallest fluctuations in the ethylene content of the atmosphere and thus recognize very early changes in the ripening process of the stored or transported products.

With this high detection sensitivity, it is possible to verify changes in the ethylene production rate of the plant products at a time where the present ethylene concentrations in the storage room do not yet have a physiological effect on the fruit, thus making it possible to react quickly to changes in the ripening process by changing the composition of the atmosphere. In that way, the knowledge of the "complete" set of data of a normally progressing ripening allows the identification of the triggering moment for the change in the metabolism as well as a prediction of the further course of the starting metabolic processes, so that it can be remedied, for example, before auto-catalytic processes are triggered.

A sorting of the plant products according to their degree of ripeness can also be performed with the photo-acoustic measuring method from the time they are stored. The high sensitivity of the sensor promises an economically high fruit output even with the examination of individual fruits.

The following example of the course of the ethylene production rate with bananas shows that the knowledge of said ethylene production rate is required for optimal storage.

Figure 3:
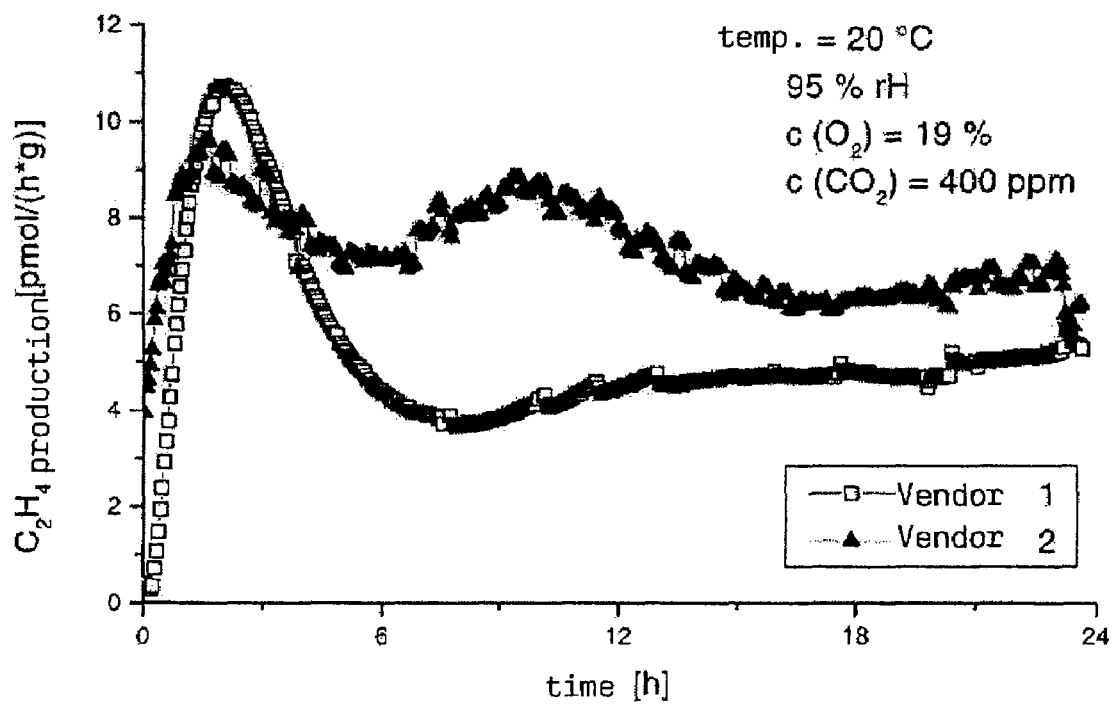
FIG. 3 shows the timely progression of the ethylene production rate of bananas with the same degree of ripeness, but with different pre-treatment.

FIG. 3 shows the timely progression of the ethylene production rate of bananas with the same degree of ripeness, but with different pre-treatment. The bananas from Vendor 1 were pretreated such with ethylene induction that they are ready for sale after 9 to 11 days. With the bananas from Vendor 2, the ripening process was induced strongly enough with exogenous ethylene that the fruit is ripe within approximately 3 to 6 days.

The bananas from Vendor 1 achieve a maximum production rate of about 11 pmol/(h*g) after almost 3 hours following storage. It can be attributed to the adaptation of the fruit to the new ambient conditions (defined air flow of 2 liters per hours, high relative air humidity of 95% at 20° C. and an $O_2$-concentration of 19% and a $CO_2$-concentration of 400 ppm). Six hours after storage, the production rate then reaches a relative minimum of about 4 pmol/(h*g) and increases slowly and steadily as time progresses. This steady increase in the production rate can be attributed to the ripening process that is underway.

With the bananas from Vendor 2, a maximum production rate of about 10 pmol/(h*g) after about 2 hours of storage is noted. It can be attributed to an adaptation of the fruit to the new ambient conditions as well (defined air flow of 2 liters per hour, high relative air humidity of 95% at 20° C. and an $O_2$-concentration of 19% and a $CO_2$-concentration of 400 ppm). The second maximum with the bananas from Vendor 2 after about 9 hours with a production rate of about 9 pmol/(h*g) indicates that there are other processes underway in the fruit. The production rate does not reach a relative minimum of about 7 pmol/(h*g) until 15 hours following storage and slowly continues to increase as time progresses. This steady increase of the production rate can be again attributed to the ripening process that is underway.

Figure 4:
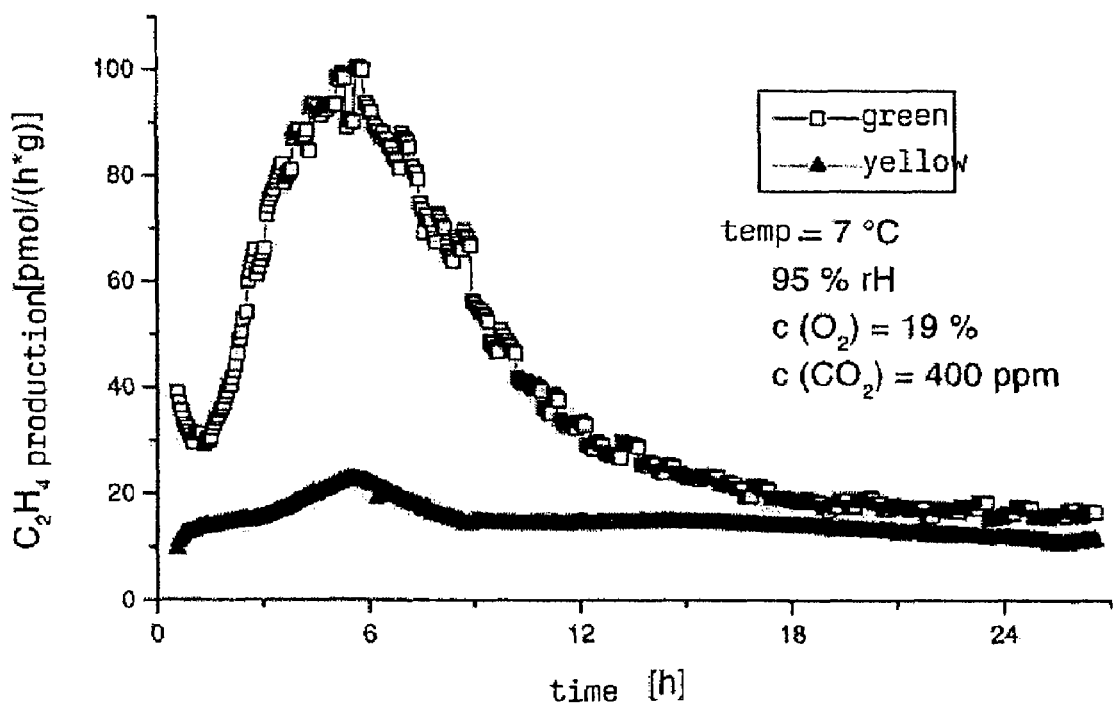
FIG. 4 shows the course of an ethylene production rate of bananas with various degrees of ripeness.

FIG. 4 shows the course of an ethylene production rate of bananas with various degrees of ripeness, including yellow, very ripe bananas, and green, unripe bananas. They are stored at a reduced storage temperature of 7° C.; the remaining storage parameters correspond to the parameters relative to Illustration 1.

A widespread adaptation peak can be noted with the ripe as well as the unripe bananas, which does not reach a maximum of the production until after about 6 hours. The maximum for the unripe bananas is at about 100 pmol/(h*g) and that of the unripe bananas is about 25 pmol/(h*g). The width of the adaptation peak can be attributed to a reduced enzyme activity at the lower temperatures.

These measurements show how strongly the fruit (in this case bananas) reacts to a change of ambient conditions with an increased production of ethylene, or that it takes up to 6 hours until the adaptation peak has decayed. Thus, the measurement of the ethylene production rate should be performed after a new balance value has been achieved, and most of all under comparable conditions once the ethylene emission has decayed due to the mechanical load and treatment.

Thus, this results in the following course for the storage of fruit in a storage room with a sorting of the fruit according to degree of ripeness:

a) Conventional treatment of the fruit (washing, sorting according to size, etc.) and intermediate storage;
b) Setting known empirical values for a controlled atmosphere in the storage room;
c) After the increased ethylene production of the fruit caused by is adaptation to the new environment and/or by mechanical stress or injuries has decayed, the storage parameters can be adapted to the degree of ripeness of the products stored in the storage space, or the ethylene production rate for individual fruits or plants can be determined with a sensor, and they can be distributed to rooms/containers with respective ideal storage parameters corresponding to their specific production rate.

As far as storage of the fruit is continued in the same storage space after the decay of the treatment stress, the air in the storage rooms/containers should always be replaced with ethylene-free air so as not to maintain any effects (induction of ripening) because of an increased ethylene concentration.

The invention is explained in greater detail in the following by means of two illustrations. FIG. 1 shows a control system for a storage space where the climate in the storage space was measured through sensors for temperature 1, air humidity 2, oxygen concentration 3, carbon dioxide concentration 4, the concentration of ethylene 5 and the concentration of other gases such as ethane, ethanol or acetaldehyde, and then processed in a control module. The optimal climate parameters are determined from the measuring data and adjusted through the controls a, b to control the temperature and the humidity, as well as the controls c, d, e, to control the concentration of oxygen, nitrogen and carbon dioxide, and f for the concentration of other gases in the atmosphere of the storage space.

Figure 2:
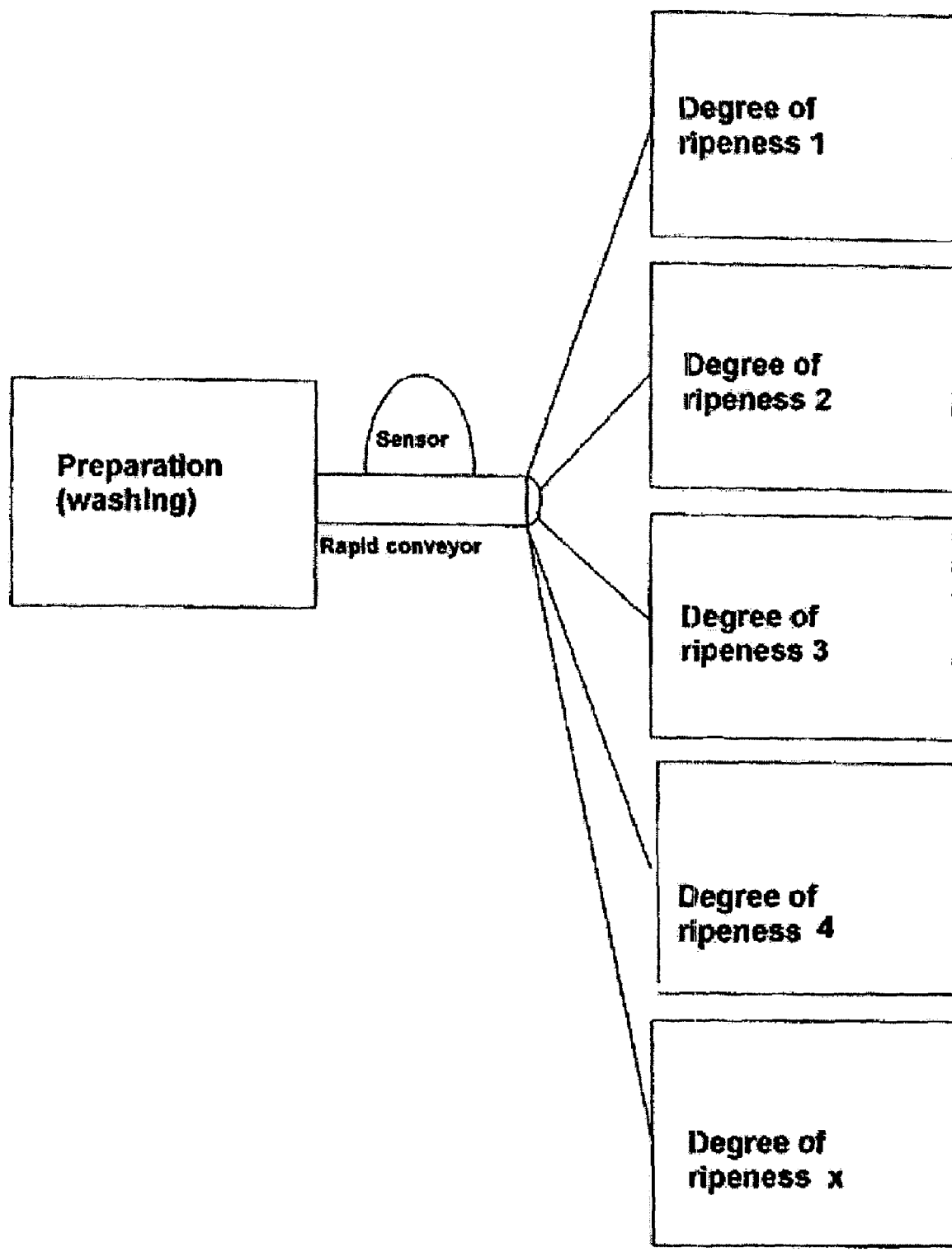
FIG. 2 shows a process description for the storage of plant products with varying degrees of ripeness.

FIG. 2 shows a process description for the storage of plant products with varying degrees of ripeness, where in the first step the plant products are prepared for storage. The preparation, for example, can consist of a simple washing of the plant products, but a climatic pretreatment, such as a treatment with exogenous ethylene, is also possible. Then the degree of ripeness of individual plant products is determined and the plant products are sorted into a chamber with climate conditions that are optimal for the specific degree of ripeness.

The invention claimed is:

1. A method of adjusting a controlled atmosphere for the storage of plant products in at least one storage or transport space, comprising:
   a) measuring a concentration of a trace gas at least twice at different times, wherein the trace gas is produced by the plant products, and wherein the trace gas represents less than 1% of the controlled atmosphere;
   b) determining a production rate, wherein the production rate comprises the degree of change of the concentration of the trace gas from at least two measurements of the concentration of the trace gas taken at different times; and
   c) adjusting the composition of the controlled atmosphere according to the production rate.

2. The method in accordance with claim 1, characterized in that the degree of change in the concentration of the $C_2H_4$-concentration is determined.

3. The method in accordance with claim 1, characterized in that the degree of change in the concentration of the $C_2H_5OH$-concentration is determined.

4. The method in accordance with claim 1, characterized in that the degree of change in the concentration of the $C_2H_6$-concentration is determined.

5. The method in accordance with claim 1, characterized in that the degree of change in the concentration of acetaldehyde is determined.

6. The method in accordance with claim 1, characterized in that the $CO_2$-concentration in the controlled atmosphere is not elevated artificially and the degree of change in the concentration of the $CO_2$-concentration is determined.

7. The method in accordance with claim 1, characterized in that the $CO_2$-concentration, the $O_2$-concentration, the room temperature and/or the air humidity are controlled.

8. The method in accordance with claim 1, characterized in that the $C_2H_4$-concentration in the controlled atmosphere is controlled.

9. The method in accordance with claim 1, characterized in that plant products with the same degree of ripeness are stored in spatial proximity to one another.

10. The method in accordance with claim 9, characterized in that the individual degree of ripeness of individual plant products is determined continually or intermittently or a mean degree of ripeness of parts of a load in the storage space is determined.

11. The method in accordance with claim 9, characterized in that the products are sorted according to their degree of ripeness during storage.

12. The method in accordance with claim 9, characterized in that the plant products with the same degree of ripeness are distributed to respective chambers and/or storage spaces having an atmosphere that is optimal for said plant products.

13. The method in accordance with claim 1, characterized in that a gas analysis method based on the photo-acoustic effect is used to determine the degree of change in the concentration of trace gases.

14. The method in accordance with claim 2, characterized in that the degree of change in the concentration of the $C_2H_5OH$-concentration is determined.

15. The method in accordance with claim 14, characterized in that the degree of change in the concentration of the $C_2H_6$-concentration is determined.

16. The method in accordance with claim 15, characterized in that the degree of change in the concentration of acetaldehyde is determined.

17. The method in accordance with claim 16, characterized in that a gas analysis method based on the photo-acoustic effect is used to determine the degree of change in the concentration of trace gases.

18. The method in accordance with claim 17, characterized in that plant products with the same degree of ripeness are stored in spatial proximity to one another.

19. The method of claim 1 further comprising:
   a) comparing the production rate to a known pattern of changes in concentrations of one or more trace gases;
   b) determining if the production rate coincides with the known pattern;
   c) in response to the determining step, retrieving a set of control variables associated with the known pattern; and
   d) using the control variables to adjust the composition of the controlled atmosphere.

20. A system for regulating a controlled atmosphere for plant products comprising: a device configured to adjust the controlled atmosphere based on measuring a concentration of a trace gas at least twice at different times, wherein the trace gas is produced by the plant products, and wherein the trace gas represents less than 1% of the controlled atmosphere; determining a production rate, wherein the production rate comprises the degree of change in concentration of the trace gas from at least two measurements of the concentration of the trace gas taken at different times; and adjusting the composition of the controlled atmosphere according to the production rate wherein the system farther comprises a photo-acoustic sensor coupled to the device.

21. The device of claim 20 further comprising:
   a) comparing the production rate to a known pattern of changes in concentrations of one or more trace gases;
   b) determining if the production rate coincides with the known pattern;
   c) in response to the determining step, retrieving a set of control variables associated with the known pattern; and
   d) using the control variables to adjust the composition of the controlled atmosphere.

* * * * *